United States Patent
Umemoto

(10) Patent No.: US 10,004,382 B2
(45) Date of Patent: Jun. 26, 2018

(54) DISPLAY APPARATUS

(71) Applicant: OLYMPUS CORPORATION, Tokyo (JP)

(72) Inventor: Yoshitaka Umemoto, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 0 days. days.

(21) Appl. No.: 15/194,639

(22) Filed: Jun. 28, 2016

(65) Prior Publication Data

US 2016/0302644 A1 Oct. 20, 2016

Related U.S. Application Data

(63) Continuation of application No. PCT/JP2014/081865, filed on Dec. 2, 2014.

(30) Foreign Application Priority Data

Feb. 19, 2014 (JP) .................................. 2014-029910

(51) Int. Cl.
*A61B 1/00* (2006.01)
*A61B 1/04* (2006.01)

(52) U.S. Cl.
CPC ........ *A61B 1/0005* (2013.01); *A61B 1/00006* (2013.01); *A61B 1/0016* (2013.01);
(Continued)

(58) Field of Classification Search
CPC . A61B 1/0005; A61B 1/00006; A61B 1/0016; A61B 1/00029; A61B 1/00055;
(Continued)

(56) References Cited

U.S. PATENT DOCUMENTS 6,522,906 B1 * 2/2003 Salisbury, Jr. ......... A61B 1/313
600/102
2012/0238807 A1 9/2012 Ashida et al.

FOREIGN PATENT DOCUMENTS

JP H11-332883 A 12/1999
JP 2008-272302 A 11/2008
(Continued)

OTHER PUBLICATIONS

International Preliminary Report on Patentability together with the Written Opinion from related International Application No. PCT/JP2014/081865 dated Sep. 1, 2016.
(Continued)

*Primary Examiner* — Timothy J Neal
(74) *Attorney, Agent, or Firm* — Scully, Scott, Murphy & Presser, P.C.

(57) ABSTRACT

A display apparatus for a living body insertable apparatus includes an inserting unit configured to be inserted into a living body, and a power unit configured to generate a propulsive force for the inserting unit in the living body. The display apparatus includes a driving force detector, a display calculator, and a display controller. The driving force detector acquires a value relating to a driving force of the power unit. The display calculator determines a display area of a gauge configured to have the display area varying according to the driving force, based on the value. The display controller outputs a signal to display the gauge on a display device.

5 Claims, 16 Drawing Sheets

(52) U.S. Cl.
CPC ...... *A61B 1/00029* (2013.01); *A61B 1/00045* (2013.01); *A61B 1/00156* (2013.01); *A61B 1/00055* (2013.01)

(58) Field of Classification Search
CPC ............ A61B 1/00045; A61B 1/00048; A61B 1/00133
See application file for complete search history.

(56) References Cited

FOREIGN PATENT DOCUMENTS

| | | |
|---|---|---|
| JP | 2009-153785 A | 7/2009 |
| JP | 2012-191978 A | 10/2012 |
| WO | 2010/090059 A1 | 8/2010 |

OTHER PUBLICATIONS

International Search Report dated Feb. 24, 2015 issued in PCT/JP2014/081865.
Extended Supplementary European Search Report dated Oct. 11, 2017 in European Patent Application No. 14 88 3411.2.

\* cited by examiner

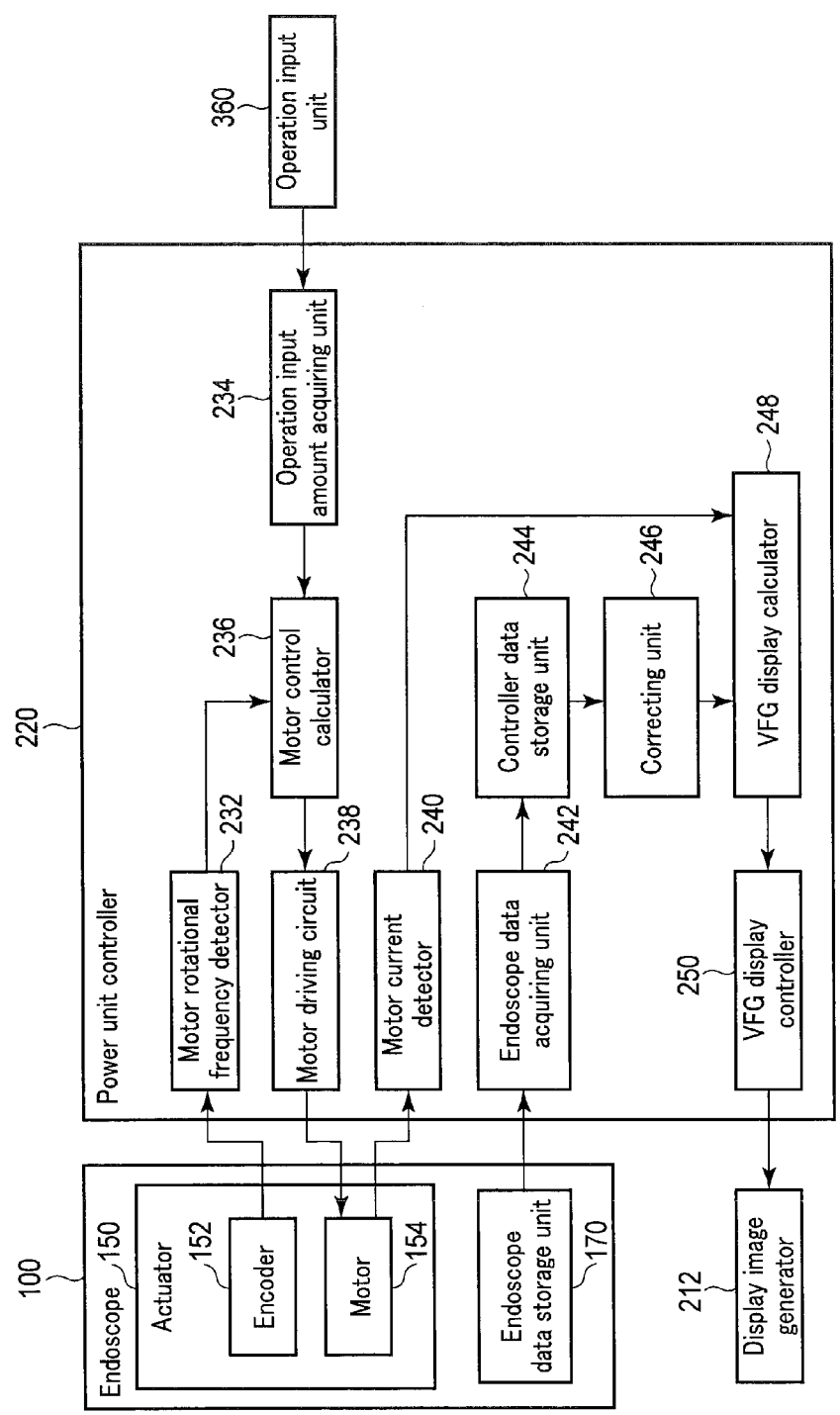
F I G. 2

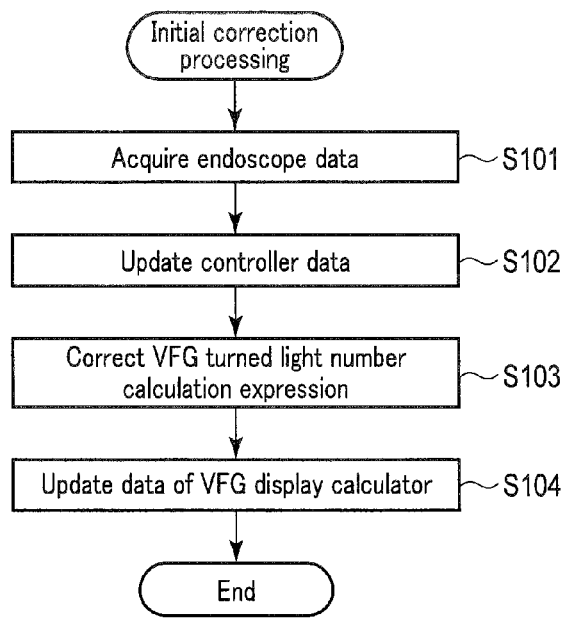
F I G. 4
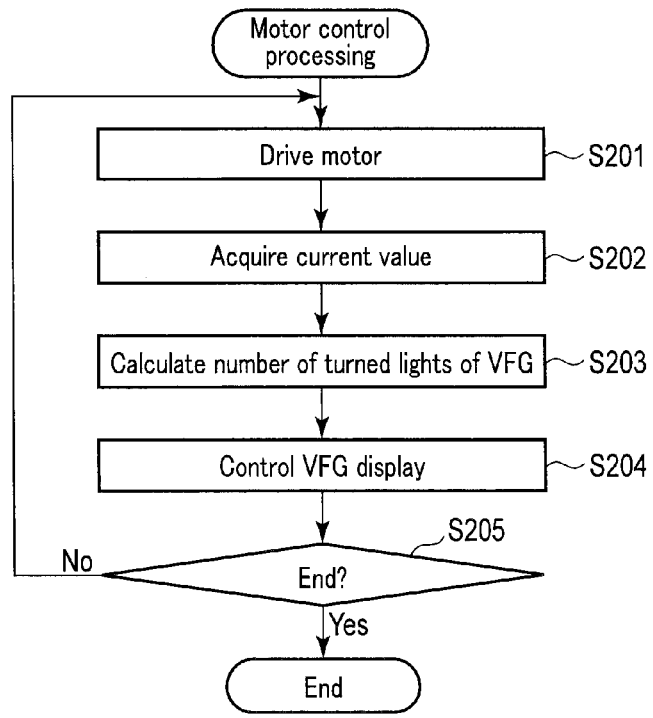
F I G. 5

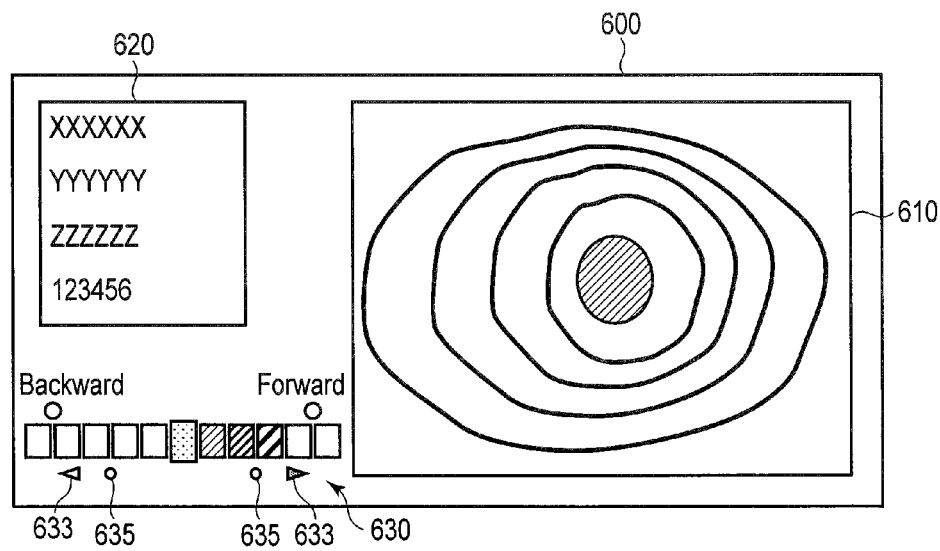
F I G. 6A
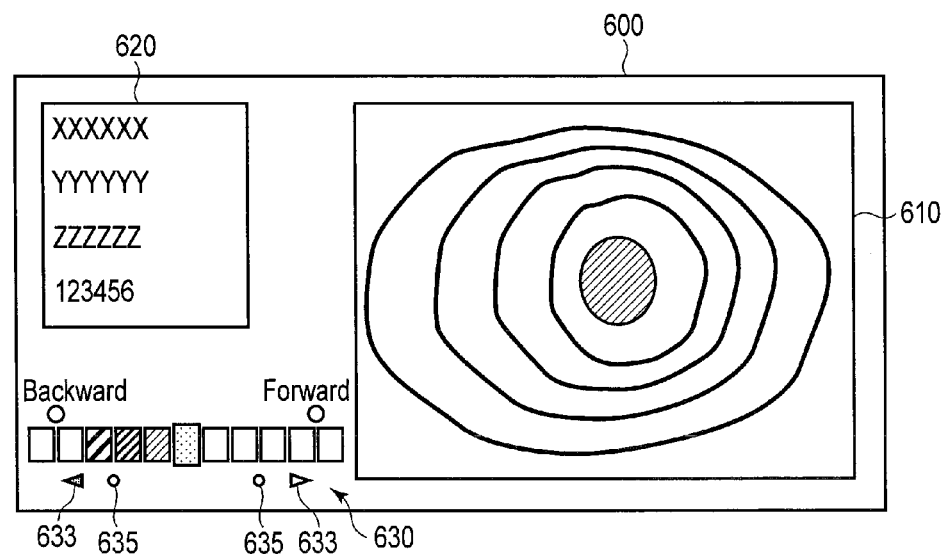
F I G. 6B

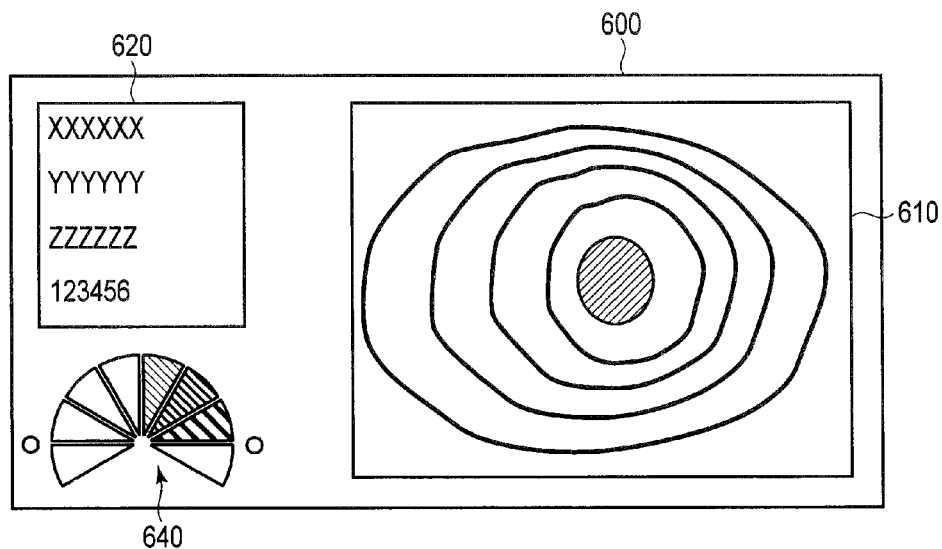
F I G. 7A
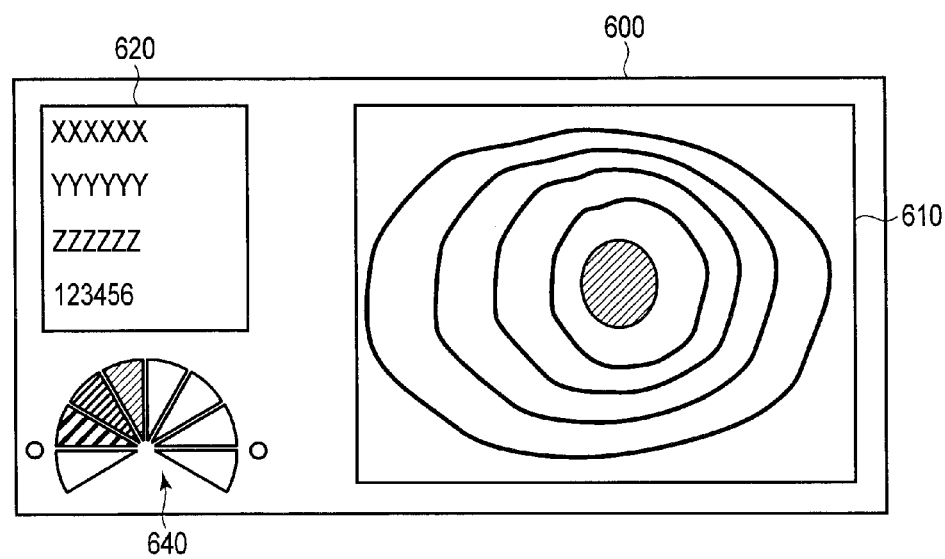
F I G. 7B

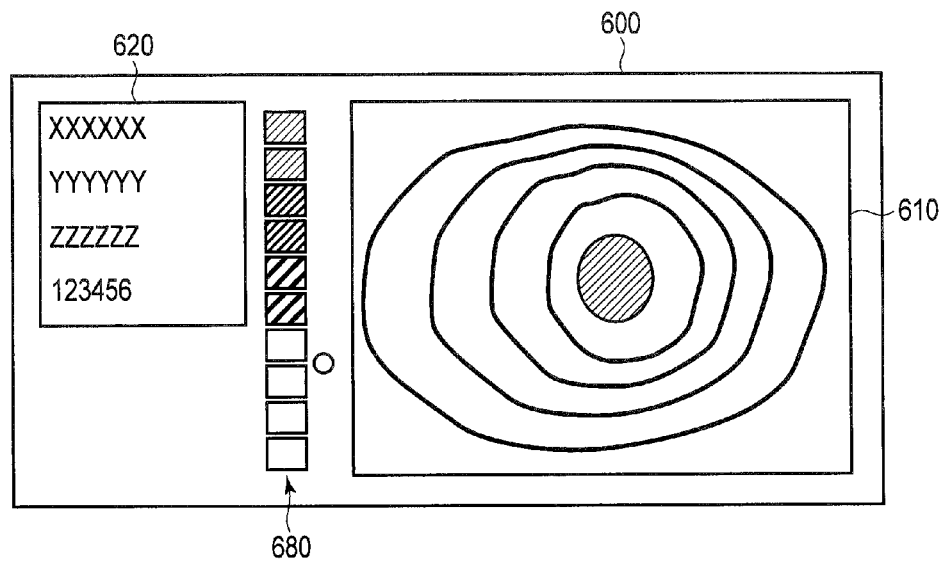
F I G. 11A
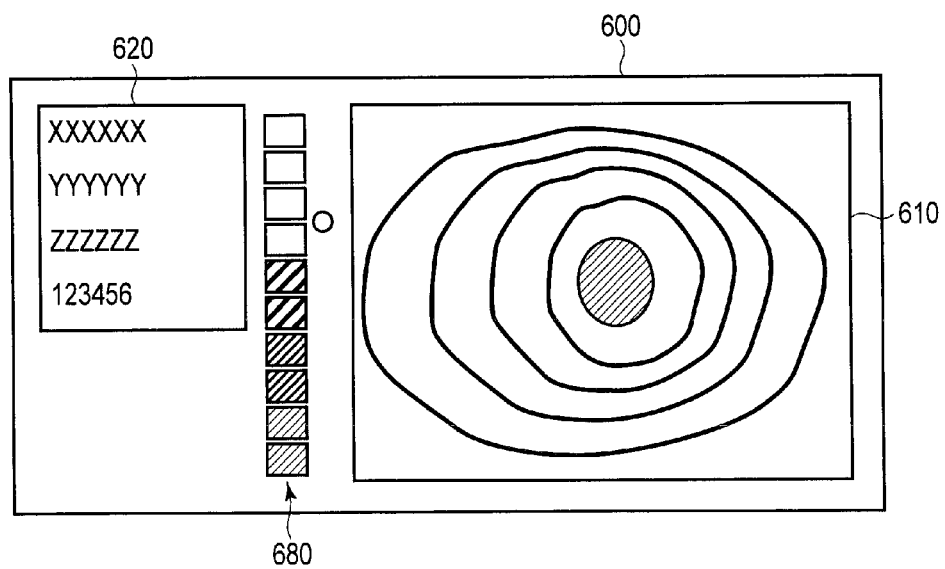
F I G. 11B

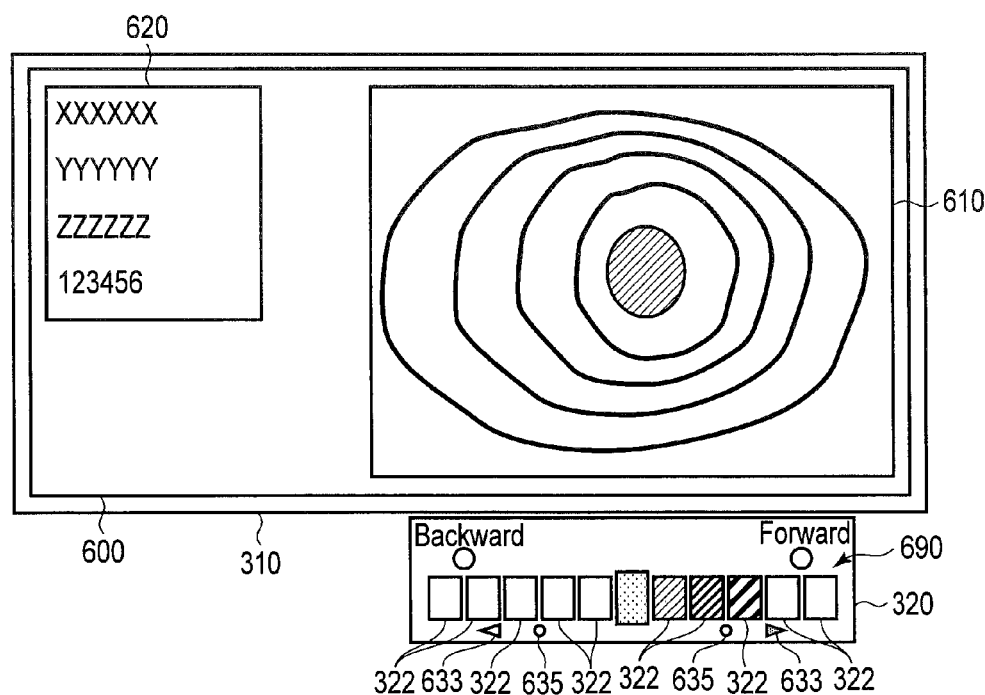
F I G. 12A

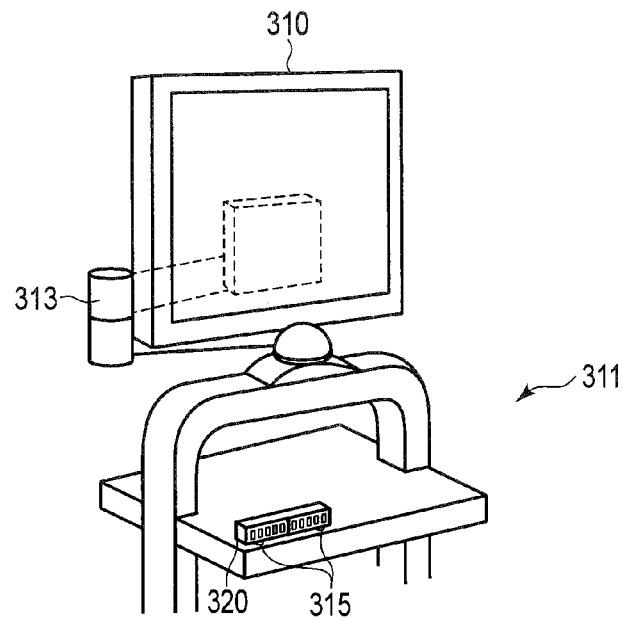
F I G. 14A
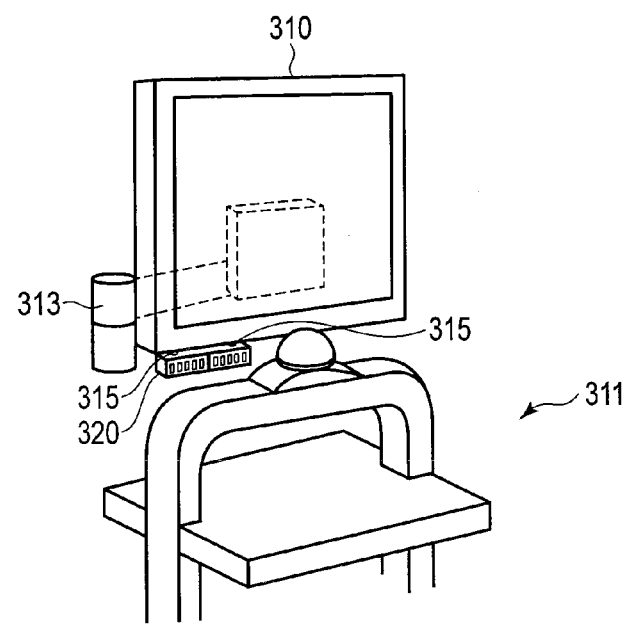
F I G. 14B

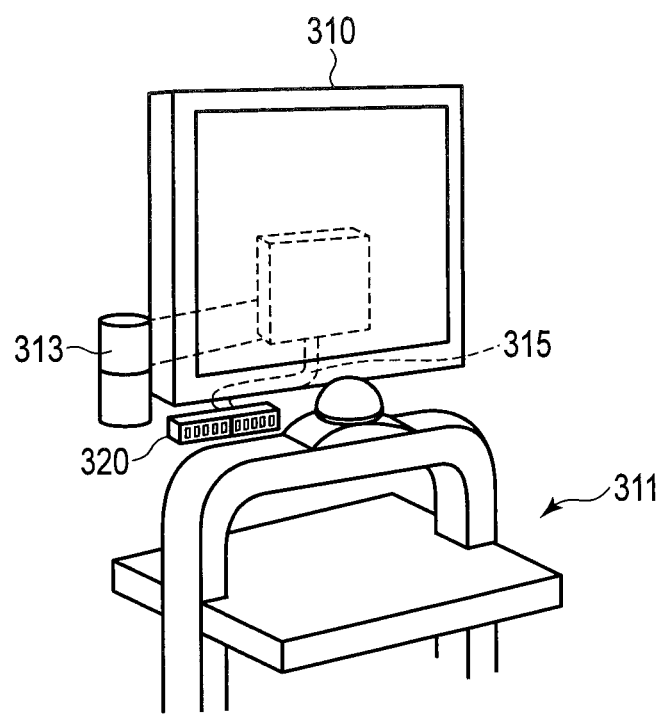
F I G. 14C

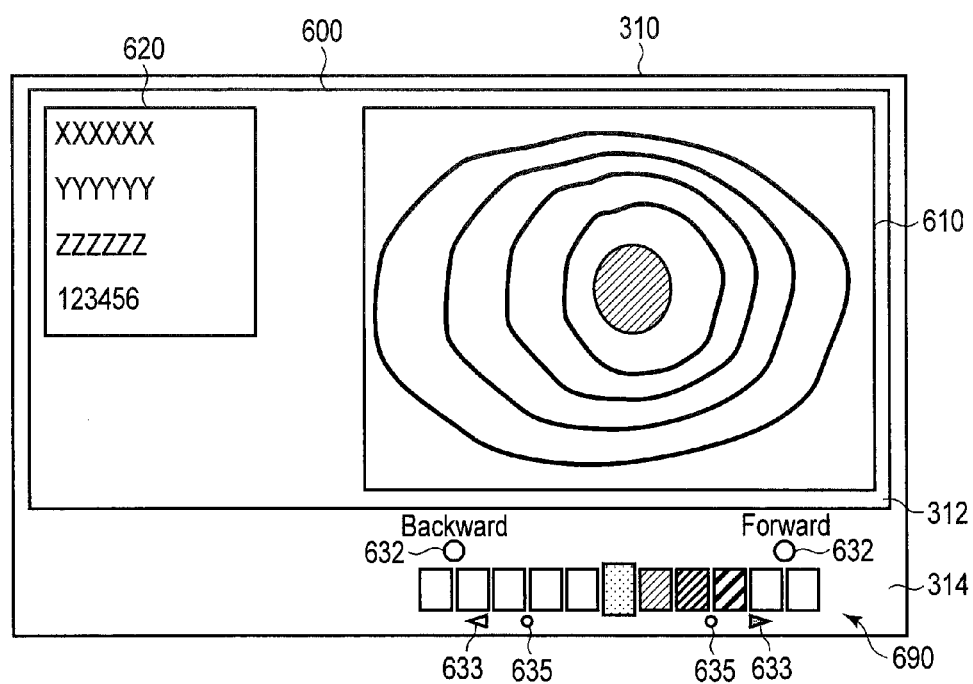
F I G. 15A

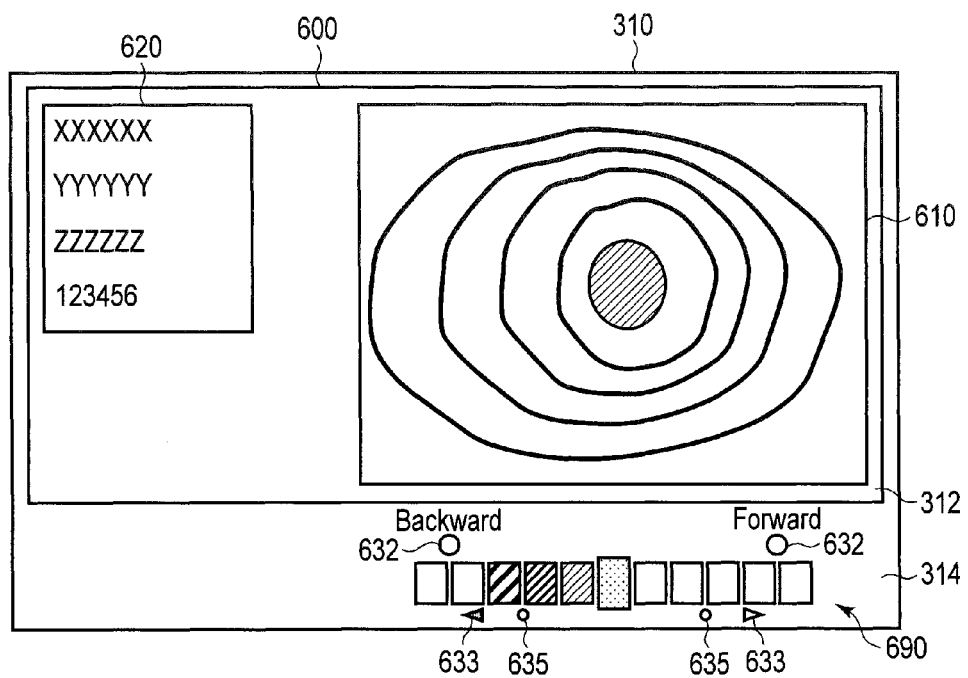
F I G. 15B

DISPLAY APPARATUS

CROSS-REFERENCE TO RELATED APPLICATIONS

This application is a Continuation Application of PCT Application No. PCT/JP2014/081865, filed Dec. 2, 2014 and based upon and claiming the benefit of priority from prior Japanese Patent Application No. 2014-029910, filed Feb. 19, 2014, the entire contents of all of which are incorporated herein by reference.

BACKGROUND OF THE INVENTION

1. Field of the Invention

The present invention relates to a display apparatus for an apparatus that is configured to be inserted into a living body.

2. Description of the Related Art

For example, apparatuses that are inserted into a living body, such as endoscopes, are generally known. For example, Japanese Patent Application Publication No. 2012-191978 discloses an endoscope system in which a propulsion mechanism is added to the living body insertable apparatus. Japanese Patent Application Publication No. 2012-191978 discloses an endoscope inspection system in which driving information such as the moving speed of the self-propulsion apparatus is displayed simultaneously with display of the observed image.

BRIEF SUMMARY OF THE INVENTION

According to an aspect of the invention, a display apparatus for a living body insertable apparatus includes an inserting unit configured to be inserted into a living body, and a power unit configured to generate a propulsive force for the inserting unit in the living body. The display apparatus includes a driving force detector which acquires a value relating to a driving force of the power unit; a display calculator which determines a display area of a gauge configured to have the display area varying according to the driving force, based on the value; and a display controller which outputs a signal to display the gauge on a display device.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 2 is a block diagram illustrating a schematic configuration example according to a power unit controller according to a first embodiment;

FIG. 4 is a flowchart illustrating a schematic example of initial correction processing according to the first embodiment;

FIG. 5 is a flowchart illustrating a schematic example of motor control processing according to the first embodiment;

FIG. 6A is a diagram illustrating a schematic example of a display image according to a first modification of the first embodiment;

FIG. 6B is a diagram illustrating a schematic example of the display image according to the first modification of the first embodiment;

FIG. 7A is a diagram illustrating a schematic example of a display image according to a second modification of the first embodiment;

FIG. 7B is a diagram illustrating a schematic example of the display image according to the second modification of the first embodiment;

FIG. 11A is a diagram illustrating a schematic example of a display image according to a sixth modification of the first embodiment;

FIG. 11B is a diagram illustrating a schematic example of the display image according to the sixth modification of the first embodiment;

FIG. 12A is a diagram illustrating a schematic example of a display image and a display device displaying a visual force gauge according to a second embodiment;

FIG. 14A is a diagram illustrating an example of arrangement of the display device according to the second embodiment;

FIG. 14B is a diagram illustrating an example of arrangement of the display device according to the second embodiment;

FIG. 14C is a diagram illustrating an example of arrangement of the display device according to the second embodiment;

FIG. 15A is a diagram illustrating a schematic example of a display image and a monitor including a visual force gauge according to a modification of the second embodiment; and FIG. 15B is a diagram illustrating a schematic example of the display image and the monitor including the visual force gauge according to the modification of the second embodiment.

DETAILED DESCRIPTION OF THE INVENTION

First Embodiment

Figure 1:
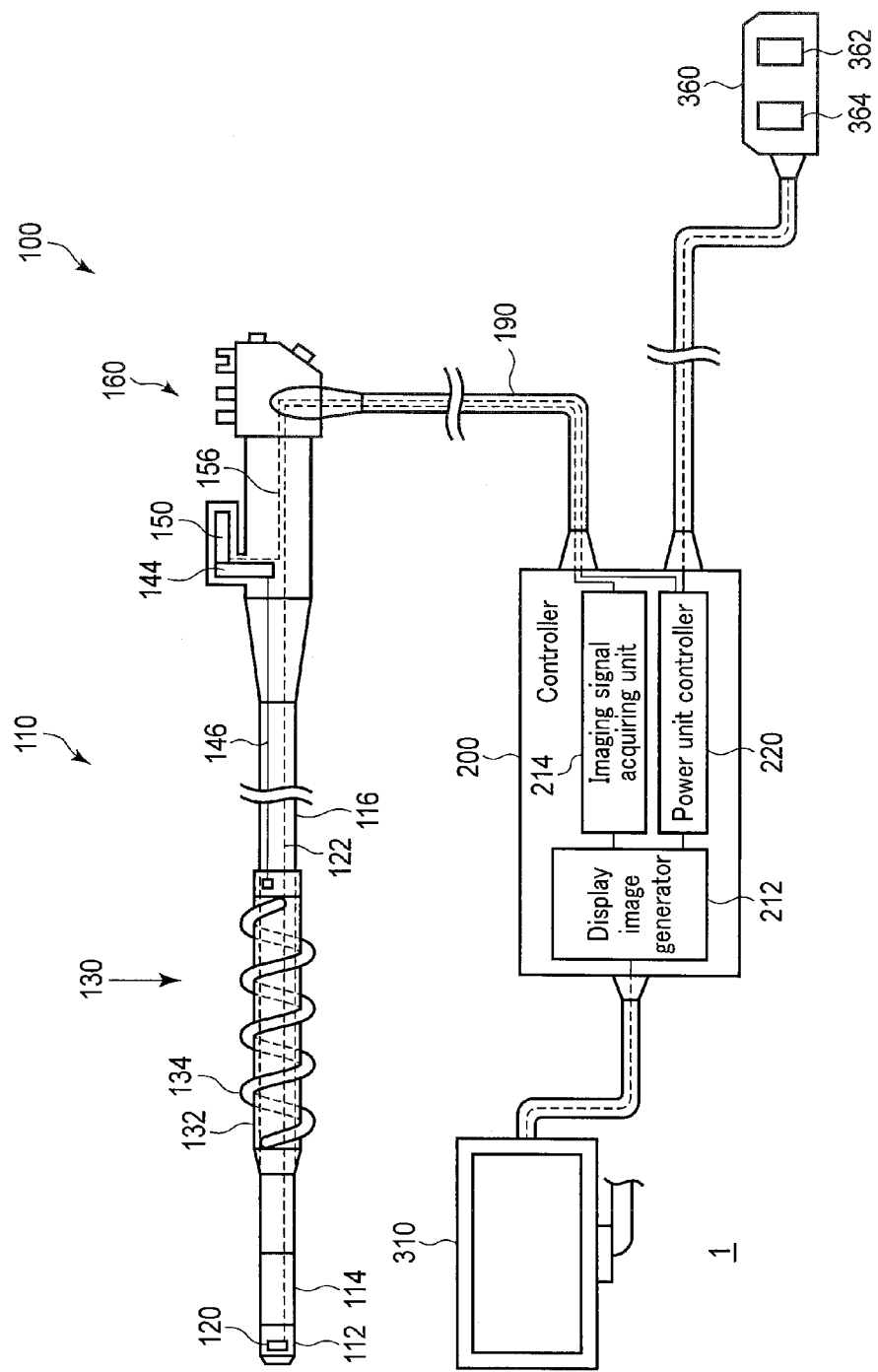
FIG. 1 is a diagram illustrating a schematic configuration example of a living body insertable apparatus according to embodiments.

The following is explanation of a first embodiment of the present invention with reference to drawings. FIG. 1 illustrates a schematic configuration of a living body insertable apparatus 1 according to the first embodiment. As illustrated in FIG. 1, the living body insertable apparatus 1 includes an endoscope 100, a controller 200, a monitor 310, and an operation input unit 360. The endoscope 100 includes an inserting unit 110 having an elongated shape and configured to be inserted into a living body. The endoscope 100 also includes an operating unit 160 to perform various operations of the endoscope 100. The operating unit 160 is held by the user. The distal end side of the inserting unit 110 is referred to as the distal end direction, and the side of the operating unit 160 is referred to as the proximal end side. The operating unit 160 of the endoscope 100 is connected with the controller 200 through a universal cable 190.

The inserting unit 110 includes a distal end hard portion 112 provided on the most distal end side, a bending section 114 provided on the proximal end side of the distal end hard portion 112, and a insertion tube 116 provided on the proximal end side of the bending section 114. The bending section 114 is configured to actively bend in accordance with rotation of an operating knob (not illustrated) provided on the operating unit 160. The insertion tube 116 is passively curved by an external force.

The distal end hard portion 112 is provided with an imaging element 120. The imaging element 120 generates an image signal based on a subject image on the distal end side of the inserting unit 110. The image signal acquired by the imaging element 120 is transmitted to the controller 200 via an imaging signal line 122 extending through the inserting unit 110 and the universal cable 190. The distal end hard portion 112 is also provided with an illumination window (not illustrated) to illuminate the subject. The illumination window is connected with a light guide (not illustrated) extending from the controller. Light emitted from a light source provided in the controller is guided by the light guide, and emitted from the illumination window. The subject is illuminated with the light emitted from the illumination window. The distal end hard portion 112 is also provided with an opening portion of a treatment tool channel tube through which a treatment tool such as forceps is inserted.

The insertion tube 116 of the inserting unit 110 is provided with a power unit 130. The power unit 130 includes a cylindrical attachment unit 132 that is provided around the insertion tube 116 to be rotatable around the longitudinal axis of the insertion tube 116. A fin 134 is provided on an external circumferential surface of the attachment unit 132. The fin 134 is provided in a spiral shape, with the longitudinal axis of the attachment unit 132 serving as the center. The fin 134 is rotated in accordance with rotation of the attachment unit 132.

The attachment unit 132 is connected with an actuator 150 provided in the operating unit 160 via a gear in a gear box 144 and a drive shaft 146. When the actuator 150 is operated by an operation using the operating input unit 360, the driving force thereof is transmitted by the gear in the gear box 144 and the drive shaft 146. As a result, the attachment unit 132 and the fin 134 are rotated clockwise and counterclockwise around the longitudinal axes thereof.

When the attachment unit 132 and the fin 134 are rotated in a state where the fin 134 is in contact with a wall portion such as a lumen wall, the propulsive force toward the distal end side or the proximal end side acts on the inserting unit 110. For example, in the small intestine or the large intestine, the fin pushes against a fold existing on the internal wall of the small intestine or the large intestine, and thereby a propulsive force acts on the inserting unit 110. Such a propulsive force improves the insertability and extractability of the inserting unit 110 in the lumen.

The monitor 310 is an ordinary display device such as a liquid crystal display. The operation input unit 360 is, for example, a foot switch. The operation input unit 360 includes a first input module 362 and a second input module 364 each of which is formed of a switch or the like. The living body insertable apparatus 1 is configured to operate the actuator 150 such that the fin 134 is rotated clockwise, for example, when the first input module 362 is turned on. The living body insertable apparatus 1 is also configured to operate the actuator 150 such that the fin 134 is rotated counterclockwise, for example, when the second input module 364 is turned on. As a result, the inserting unit 110 moves forward toward the distal end side when the first input module 362 is turned on, and the inserting unit 110 moves backward toward the proximal end side when the second input module 364 is turned on.

The controller 200 controls the units in the living body insertable apparatus 1. The controller 200 includes a display image generator 212, and an imaging signal acquiring unit 214 to acquire a signal of an image acquired by the imaging element 120 of the endoscope 100. The imaging signal acquiring unit 214 acquires an image signal from the imaging element 120, performs necessary image processing on the image, and outputs the image signal to the display image generator 212. The display image generator 212 generates an image signal corresponding to the image to be displayed on the monitor 310, based on the image signal acquired from the imaging signal acquiring unit 214 and information relating to the living body insertable apparatus 1 described later. The display image generator 212 outputs the generated image signal to the monitor 310, to display the image on the monitor 310.

The controller 200 also includes a power unit controller 220 to control operations of the power unit 130. The actuator 150 is connected with the power unit controller 220 via an actuator current signal line 156. The power unit controller 220 is connected with the display image generator. The power unit controller 220 generates an image signal to display information as to the driving force relating to the power unit 130 on the monitor 310. The power unit controller 220 outputs the image signal to the display image generator 212.

The configuration relating to the power unit controller 220 will be explained hereinafter with reference to the block diagram of FIG. 2. The actuator 150 provided in the endoscope 100 includes an encoder 152 and a motor 154. The motor 154 is a power source that drives the power unit 130. The encoder 152 detects a driving amount of the motor 154.

The endoscope 100 includes an endoscope data storage unit 170. The endoscope data storage unit 170 stores information relating to the endoscope 100. The endoscope data storage unit 170 stores, for example, torque limiter values of clockwise rotation and counterclockwise rotation of the motor 154.

The power unit controller 220 includes a motor rotational frequency detector 232, an operation input amount acquiring unit 234, a motor control calculator 236, a motor driving circuit 238, a motor current detector 240, an endoscope data acquiring unit 242, a controller data storage unit 244, a correcting unit 246, a visual force gauge (VFG) display calculator 248, and a VFG display controller 250.

The motor rotational frequency detector 232 is connected with the encoder 152, and detects the rotational frequency of the motor 154. The motor rotational frequency detector 232 outputs the detected rotational frequency of the motor to the motor control calculator 236. The operation input amount acquiring unit 234 acquires an input amount to the operation input unit 360 from the operation input unit 360. The operation input amount acquiring unit 234 outputs the acquired input amount to the motor control calculator 236.

The motor control calculator 236 performs various calculations relating to driving of the motor 154. Specifically, the motor control calculator 236 calculates the driving amount of the motor 154, based on the information relating to the operation input amount acquired from the operation input amount acquiring unit 234 and the information relating to the motor rotational frequency acquired from the motor rotational frequency detector 232. Based on the calculated driving amount, the motor control calculator 236 calculates a power value to be input to the motor, and outputs the power value to the motor driving circuit 238. The motor driving circuit 238 operates the motor 154, based on the power value input from the motor control calculator 236.

The motor current detector 240 detects the current value input to the motor 154. The motor current detector 240 functions as a driving force detector that acquires a value relating to the driving force of the power unit. The motor current detector 240 outputs the acquired current value to the VFG display calculator 248.

The endoscope data acquiring unit 242 acquires information relating to the endoscope from the endoscope data storage unit 170. The endoscope data acquiring unit 242 outputs the acquired information relating to the endoscope 100 to the controller data storage unit 244. The controller data storage unit 244 stores controller data serving as information relating to the controller 200. The controller data storage unit 244 updates the controller data, based on the information relating to the endoscope 100 and acquired by the endoscope data acquiring unit 242. The controller data storage unit 244 outputs the controller data to the correcting unit 246. The correcting unit 246 corrects a calculation expression relating to the VFG display, based on the controller data. The correcting unit 246 outputs the corrected calculation expression to the VFG display calculator 248.

The VFG display calculator 248 calculates a value relating to the VFG display, based on the current value flowing through the motor 154 and acquired from the motor current detector 240, and the calculation expression acquired from the correcting unit 246. The gauge of the VFG is configured to have a display area that varies according to the current value. The VFG display calculator 248 outputs the calculated value relating to the VFG display to the VFG display controller 250. The VFG display controller 250 generates a display signal suitable for the display image generator 212 to generate an image signal, and outputs the display signal to the display image generator 212.

The following is an explanation of operations of the living body insertable apparatus 1 according to the present embodiment. The living body insertable apparatus 1 is used for, for example, observation of the inside of the body cavity. When the living body insertable apparatus 1 is used, the user inserts the inserting unit 110 into the body of the subject, while holding the operating unit 160 by the left hand, for example, and holding the insertion tube 116 by the right hand. In addition, the user operates the operation input unit 360, which is a foot switch or the like, by foot, to rotate the fin 134 and move the inserting unit 110 forward and backward. In this state, the user operates the living body insertable apparatus 1 while viewing the monitor 310.

Figure 3A:
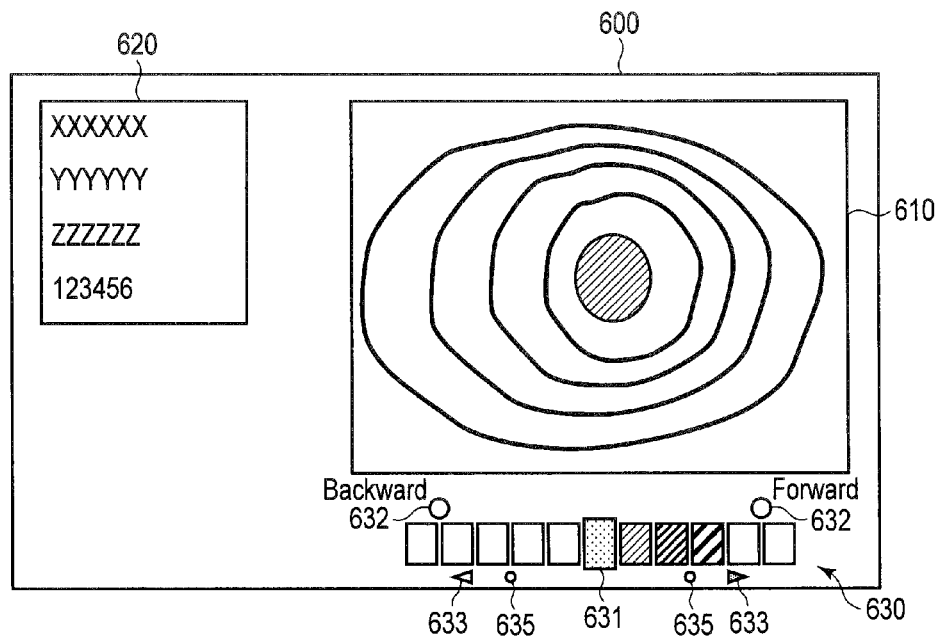
FIG. 3A is a diagram illustrating a schematic example of a display image according to the first embodiment.
Figure 3B:
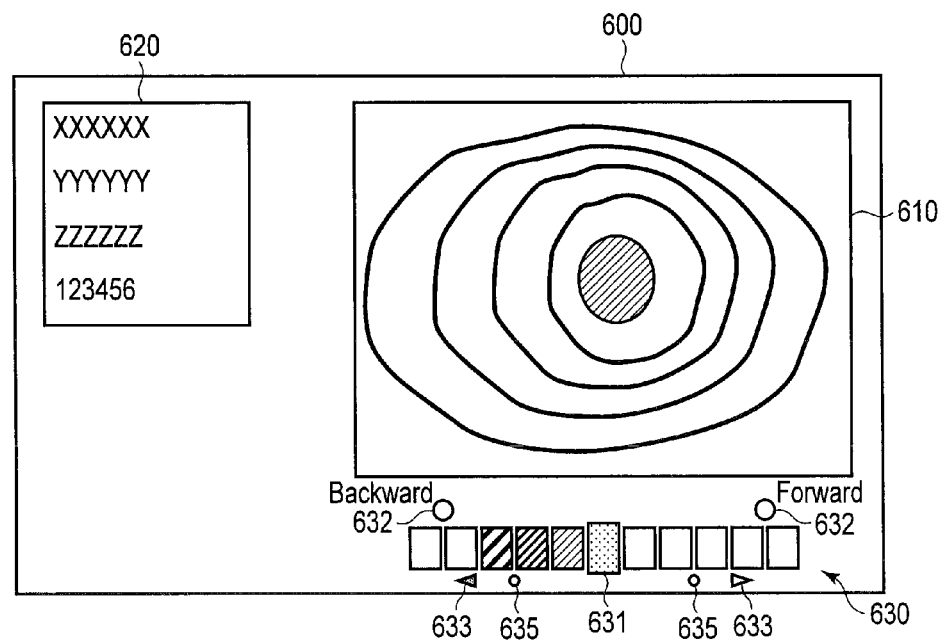
FIG. 3B is a diagram illustrating a schematic example of the display image according to the first embodiment.

In the present embodiment, a display image 600 such as illustrated in FIG. 3A and FIG. 3B is displayed on the monitor 310. For example, the upper right portion of the display image 600 includes an endoscopic image 610 imaged by the imaging element 120. The part on the left side of the endoscopic image 610 in the display image 600 includes character information 620 indicating, for example, the date and time, information of the subject, and setting information of the endoscope 100. The part under the endoscopic image 610 in the display image 610 includes a visual force gauge (VFG) 630 according to the present embodiment.

The VFG 630 indicates information relating to the torque of the motor 154, which relates to the driving force of the power unit 130. In the VFG 630 according to the present embodiment illustrated in FIG. 3A and FIG. 3B, a plurality of rectangles are arranged in the right and left direction. A rectangle disposed in the center among the rectangles is a reference rectangle 631 indicating a reference position. In the VFG 630, when the user turns on the first input module 362 to move the inserting unit 110 forward, the display form of the rectangles located on the right side of the reference rectangle 631 is changed as illustrated in FIG. 3A. An example of a change in the display form is, for example, a change in color, pattern, and/or brightness of the rectangles. Various combinations of changes in color, pattern, and brightness of the rectangles may be used as the change in the display form. The number (hereinafter referred to as the number of turned on lights of rectangles in which the display form is changed varies according to the magnitude of the torque relating to the motor 154 that drives the power unit 130. The torque can be calculated from the current value detected by the motor current detector 240. In the VFG 630, the number of turned on lights of the VFG 630 increases as the torque increases. That is, the display area indicating the output in the VFG 630 increases as the torque increases. In addition, when the user turns on the first input module 362 to move the inserting unit 110 forward, an arrow 633 located on the right side in FIG. 3A representing the moving direction of the inserting unit 110 lights up. When the user turns off the first input module 362, the arrow 633 is turned off.

In the same manner, in the VFG 630, when the user turns on the second input module 364 to move the inserting unit 110 backward, the display form of the rectangles located on the left side of the reference rectangle 631 is changed as illustrated in FIG. 3B. Also in this case, the number of turned on lights changes according to the torque of the motor 154. In addition, when the user turns on the second input module 364 to move the inserting unit 110 backward, an arrow 633 located on the left side in FIG. 3B representing the moving direction of the inserting unit 110 lights up. When the user turns off the second input module 364, the arrow 633 is turned off.

Generally, torque control is performed in the unit to move the inserting unit 110 forward or backward, such as the power unit 130 according to the present embodiment. For example, the current flowing through the motor 154 is controlled such that the fin 134 is set to a predetermined rotational speed. For this reason, for example, when a tube through which the inserting unit 110 is inserted has a stenosed portion, the current is adjusted such that a large current flows through the motor 154 when the inserting unit 110 passes through the stenosed portion. When such a large current flows, the motor 154 may break down. In addition, a large current may damage the tube through which the inserting unit 110 is inserted. The present embodiment enables the user to operate the living body insertable apparatus 1 while the user checks the VFG 630 included in the display image 600 to check the torque of the motor 154. This structure prevents breakdown of the living body insertable apparatus 1 and damage to the tube from the inserting unit 110.

In the present embodiment, the VFG 630 is provided with load indexes 632. The load indexes 632 indicate the load a load larger than which may cause any malfunction when the load is imposed on the motor 154. Accordingly, the user controls the operation of the living body insertable apparatus 1 to prevent a load larger than the load indicated by the load indexes 632 from being imposed on the motor 154. The living body insertable apparatus 1 may be controlled to stop the rotation of the motor 154 when a load larger than the load indicated by the load indexes 632 is imposed on the motor 154. As another example, the living body insertable apparatus 1 may be controlled to stop the power supply to the motor 154 to change the driving shaft of the motor 154 to a state without load, when a load larger than the load indicated by the load indexes 632 is imposed on the motor 154. To enable the user to visually recognize the state of the driving system, the living body insertable apparatus 1 may be configured to blink on and off only the rectangles on the forward side or the backward side among the rectangles of the VFG 630, when a load larger than the load indicated by the load indexes 632 is imposed on the motor 154 or when a load to light up all the rectangles of the VFG 630 is imposed on the motor 154. The living body insertable apparatus 1 may be configured to blink on and off all the rectangles of the VFG 630, when the driving system such as the motor 154 and the power unit controller 220 breaks down. In addition, in the present embodiment, as illustrated in FIG. 3A and FIG. 3B, assistant load indexes 635 are separately provided in a region holding the VFG 630 with the region where the load indexes 632 are located. The load indexes 632 and the assistant load indexes 635 can be used for different cases. For example, the load indexes 632 are used as indexes for checking the torque in the state where the inserting unit 110 is inserted into the body, and the assistant load indexes 635 are used as indexes for checking the torque when the inserting unit 110 is located outside the body. An example of the circumstance where the torque should be checked in the state where the inserting unit 110 is located outside the body is a circumstance in which the motor 154 is rotated to the maximum under a circumstance without load where the inserting unit 110 is located outside the body to check whether the rectangles of the VFG 630 light up to the positions of the assistant load indexes 635, in order to check whether the attachment unit 132 is normally attached to the insertion tube 116. Specifically, when the attachment unit 132 is in the normal attached state, the rectangles of the VFG 630 in FIG. 3A and FIG. 3B light up to the positions of the assistant load indexes 635 on both the forward side and the backward side (specifically, two rectangles light up on each of the sides). One or three rectangles lighting up on each side indicates that the attachment unit 132 is not normally attached or the system breaks down.

FIG. 3A and FIG. 3B illustrate the example where the number of rectangles indicating the magnitude of the torque in the VFG 630 is five on each of the forward side and the backward side. However, the number may be any number, such as 15 on each side, as a matter of course. FIG. 3A and FIG. 3B illustrate an example of the VFG 630 where a plurality of rectangles are arranged in a discrete manner, but the structure is not limited thereto. The adjacent rectangles may contact each other and may be continuously arranged. In this case, the VFG 630 is displayed such that the area of a portion that changes to a different color or the like in a rectangle varies. FIG. 3A and FIG. 3B illustrate the example where one load index 632 is disposed on each of the forward side and the backward side, but the number of the load indexes 632 may be any number, such as two on each side, as a matter of course.

In the present embodiment, the VFG 630 displays the torque relating to the motor 154, based on the current value acquired by the motor current detector 240. The endoscope 100 connected to the controller 200 may be changed. Specifically, various endoscopes 100 may be connected to the same controller 200, according to the use thereof and the like. In addition, even endoscopes 100 of the same type have individual variations in the structure relating to the power unit 130. Accordingly, the relation between the current value acquired by the motor current detector 240 and the torque displayed on the VFG 630 may change. For this reason, in the present embodiment, when the living body insertable apparatus 1 is turned on, initial correction corresponding to the endoscope 100 is performed, with respect to the relation between the current flowing through the motor 154 and the display of the VFG 630. The following is an explanation of initial correction processing that is performed when the power of the living body insertable apparatus 1 is turned on, with reference to the flowchart in FIG. 4.

In step S101, the endoscope data acquiring unit 242 acquires endoscope data from the endoscope data storage unit 170. The endoscope data includes individual information of the power unit 130, such as information of the torque limiter of the motor 154 to drive the power unit 130 of the endoscope 100. The endoscope data acquiring unit 242 outputs the acquired endoscope data to the controller data storage unit 244.

In Step S102, the controller data storage unit 244 updates the controller data, based on the input endoscope data. The controller data storage unit 244 outputs the updated controller data to the correcting unit 246.

In Step S103, the correcting unit 246 corrects the calculation expression to display the VFG 630. The calculation expression is an expression representing a relation between, for example, the current value acquired by the motor current detector 240 and the number of turned on lights of the VFG 630. The correcting unit 246 outputs the corrected calculation expression to the VFG display calculator 248.

In Step S104, the VFG display calculator 248 updates the data in the VFG display calculator 248 for the calculation expression input from the correcting unit 246. The initial correction processing is ended by the above. The initial correction performed like this before use enables accurate torque display, regardless of the type and individual variation of the endoscope 100.

The following is an explanation of motor control processing performed in a case when the inserting unit 110 is inserted and the power unit 130 operates, with reference to FIG. 5.

In Step S201, the motor is driven. Specifically, the motor rotational frequency detector 232 acquires the rotational frequency of the motor from the encoder 152 provided in the actuator 150. The motor rotational frequency detector 232 outputs the acquired rotational frequency to the motor control calculator 236. The motor control calculator 236 calculates a current value applied to the motor 154, based on the input rotational frequency. The motor control calculator 236 outputs the calculated current value to the motor driving circuit 238. The motor driving circuit 238 drives the motor 154, based on the input current value.

In Step S202, the motor current detector 240 acquires the value of the current flowing through the motor 154. The motor current detector 240 outputs the acquired current value to the VFG display calculator 248.

In Step S203, the VFG display calculator 248 calculates the number of turned on lights of the VFG 630, based on the calculation expression adjusted by the initial correction processing described above. The VFG display calculator 248 outputs the calculated number of turned on lights of the VFG to the VFG display controller 250.

In Step S204, the VFG display controller 250 controls the VFG display. Specifically, the VFG display controller 250 prepares image information relating to the VFG 630 to be displayed on the monitor 310, based on the number of turned on lights of the VFG input from the VFG display calculator 248. The VFG display controller 250 outputs the prepared image information to the display image generator 212. The display image generator 212 generates an image signal of the display image 600 including the VFG 630, based on the input image information, and causes the monitor 310 to display the display image 600.

In Step S205, it is determined whether the motor control processing is to be ended. When it is determined that the motor control processing is not to be ended, the processing returns to Step S201. By contrast, when it is determined that the motor control processing is to be ended, the motor control processing is ended.

As described above, the monitor 310 displays information relating to the output of the unit such as the power unit 130, as the VFG 630, the unit moving the inserting unit 110 forward or backward. The user is enabled to operate the living body insertable apparatus 1 while checking the torque of the motor 154 by checking the VFG 630. This structure prevents breakdown of the living body insertable apparatus 1 and damage to the tube serving as a target into which the living body insertable apparatus 1 is inserted.

In the present embodiment, the VFG 630 is provided adjacent to and under the endoscopic image 610. Because the user pays close attention to the endoscopic image 610, disposing the VFG 630 close to the endoscopic image 610 is effective for easy recognition of the VFG 630.

The present embodiment illustrates an example of the power unit including a spiral fin. However, the structure is not limited thereto. For example, the inserting unit 110 may be configured to move forward or backward by rotation of a belt provided in the inserting unit 110. Specifically, the present technique can be used in various living body insertable apparatuses in which the driving force by the actuator is used for moving the inserting unit 110 forward or backward.

The VFG 630 according to the present embodiment is not necessarily displayed under the endoscopic image 610, but may be displayed above the endoscopic image 610. As another example, the VFG 630 may be displayed in a vertical direction on the left side or the right side of the endoscopic image 610.

Indexes similar to the load indexes 632 are not necessarily provided to indicate the load that may cause malfunction as described above, but may be provided to indicate other loads. For example, the VFG 630 may be provided with load indexes that indicate a load that is acquired when the power unit 130 is operated in a state where the inserting unit 110 is not inserted into the tube, that is, when the power unit 130 is operated without any load, to inspect the power unit 130. In this case, when the power unit 130 is operated in inspection and the VFG indicates the load indexes, it means that the power unit 130 normally operates. In addition, load indexes may be provided as marks for the rectangles included in the VFG. For example, when 15 rectangles are arranged in the VFG, a load index may be provided for every fifth rectangle. Such marks enable the user to easily recognize the magnitude of the load. The load indexes may be arranged in various positions, for example, above or under the rectangles with a varying display form, or both of them.

The present embodiment illustrates an example of the case where the torque of the motor 154 is evaluated with a current, as a value relating to the driving force of the power unit 130, but the structure is not limited thereto. The VFG 630 may be configured to acquire a value relating to the driving force in various places relating to the power unit 130, and to display the value.

First Modification of the First Embodiment

The following is an explanation of a first modification of the first embodiment. Only differences of the first modification from the first embodiment will be explained hereinafter. The same elements will be denoted by the same reference numerals, and explanation thereof is omitted. The present modification is different from the first embodiment in the position of the VFG 630 in the display image 600. Specifically, in the present embodiment, as illustrated in FIG. 6A and FIG. 6B, a VFG 630 similar to the VFG 630 in the first embodiment is disposed in a position on the left side of the endoscopic image 610 and under the character information 620. The other structures are the same as those in the first embodiment.

The present embodiment increases the rate of the area of the endoscopic image 610 in the display image 600. Of the information included in the display image 600, that of the endoscopic image 610 is of high importance. For this reason, the endoscopic image 610 with a large area is effective for the living body insertable apparatus 1.

Second Modification of the First Embodiment

The following is an explanation of a second modification of the first embodiment. Only differences of the second modification from the first modification of the first embodiment will be explained hereinafter. The same elements will be denoted by the same reference numerals, and explanation thereof is omitted. The present modification is different from the first modification of the first embodiment in the form of the VFG in the display image 600. Specifically, as illustrated in FIG. 7A and FIG. 7B, a VFG 640 according to the present modification has a shape different from that of the VFG 630 according to the first modification of the first embodiment, although the VFG 640 is disposed in a position similar to that of the VFG 630.

As illustrated in FIG. 7A and FIG. 7B, the VFG 640 according to the present modification has a shape in which a plurality of fan-shaped pieces are arranged side by side. Also in the present modification, when the inserting unit 110 moves forward, the display form of the right fan-shaped pieces in the VFG 640 changes as illustrated in FIG. 7A.

When the inserting unit 110 moves backward, the display form of the left fan-shaped pieces in the VFG 640 changes as illustrated in FIG. 7B. The VFG 640 is configured to have the number of turned on lights that varies according to the torque applied to the motor 154. The other structures are the same as those in the first modification of the first embodiment.

The VFG 640 according to the present modification has a reduced lateral width, while the VFG 630 according to the first modification of the first embodiment has a laterally elongated shape. This structure enables effective use of the region under the character information 620 in the display image 600.

Third Modification of the First Embodiment

The following is an explanation of a third modification of the first embodiment. Only differences of the third modification from the first modification of the first embodiment will be explained hereinafter. The same elements will be denoted by the same reference numerals, and explanation thereof is omitted. The present modification is different from the first modification of the first embodiment in the form of the VFG in the display image 600. Specifically, as illustrated in FIG. 8A and FIG. 8B, a VFG 650 according to the present modification has a shape different from that of the VFG 630 according to the first modification of the first embodiment, although the VFG 650 is disposed in a position similar to that of the VFG 630.

Figure 8A:
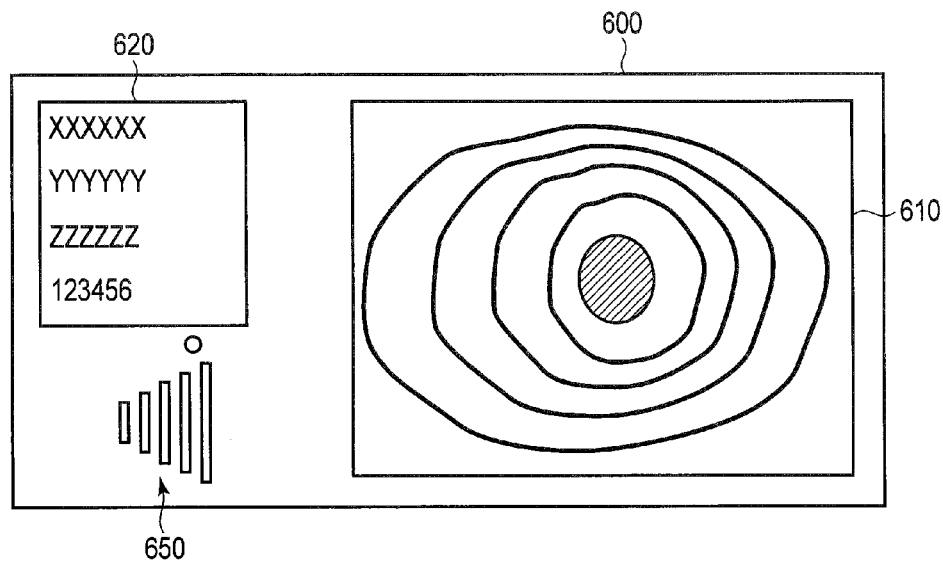
FIG. 8A is a diagram illustrating a schematic example of a display image according to a third modification of the first embodiment.
Figure 8B:
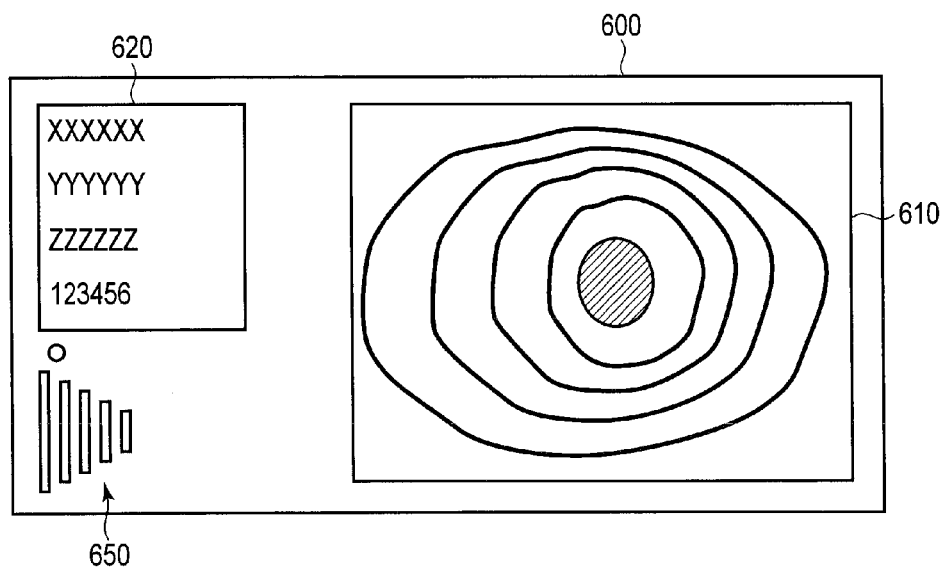
FIG. 8B is a diagram illustrating a schematic example of the display image according to the third modification of the first embodiment.

As illustrated in FIG. 8A and FIG. 8B, the VFG 650 according to the present modification has a gauge width (a vertical length in the drawings) that increases together with increased torque. In the present modification, when the first input module 362 is turned on and the inserting unit 110 is moved forward, the right gauge in the VFG 650 is displayed as illustrated in FIG. 8A. By contrast, when the second input module 364 is turned on and the inserting unit 110 is moved backward, the left gauge in the VFG 640 is displayed as illustrated in FIG. 8B. The VFG 650 is configured to vary the number of turned on lights according to the torque applied to the motor 154. The other structures are the same as those in the first modification of the first embodiment.

The VFG 650 according to the present modification enables an emphasized display of the direction and the magnitude of the torque.

The display system of the present modification in which the VFG is displayed only when the power unit 130 operates may be applicable to other embodiments and other modifications.

Fourth Modification of the First Embodiment

The following is an explanation of a fourth modification of the first embodiment. Only differences of the fourth modification from the first embodiment will be explained hereinafter. The same elements will be denoted by the same reference numerals, and explanation thereof is omitted. The present modification is different from the first embodiment in the form of the VFG in the display image 600. Specifically, as illustrated in FIG. 9A and FIG. 9B, a VFG 660 according to the present modification has a shape different from that of the VFG 630 according to the first embodiment, although the VFG 660 is disposed in a position similar to that of the VFG 630.

Figure 9A:
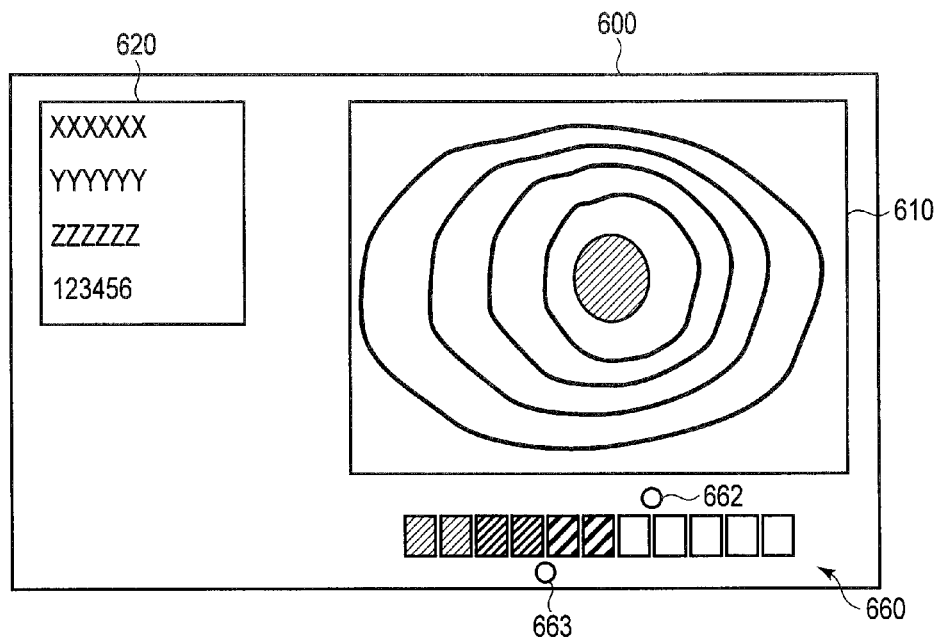
FIG. 9A is a diagram illustrating a schematic example of a display image according to a fourth modification of the first embodiment.
Figure 9B:
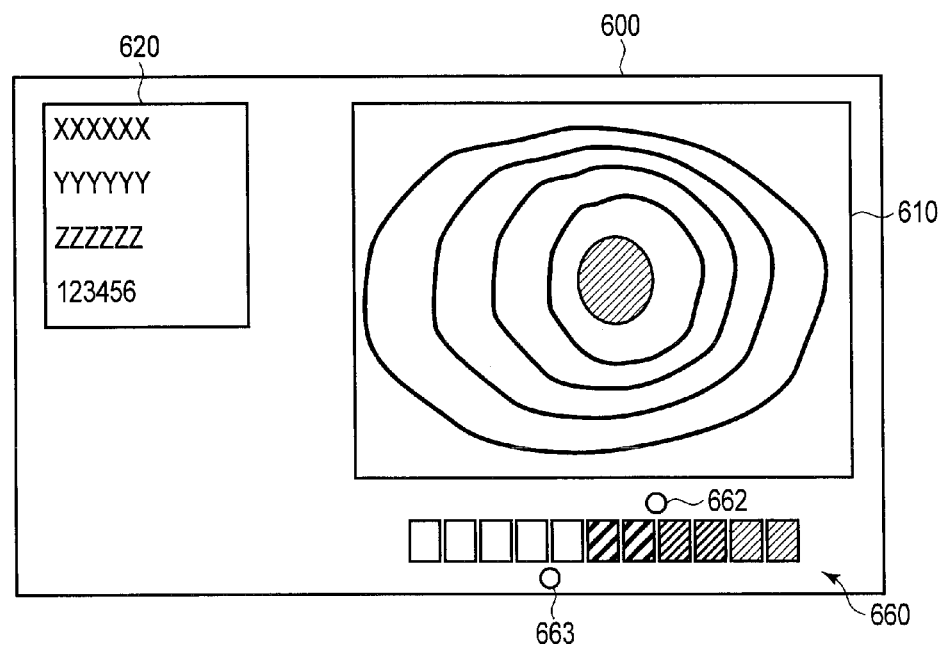
FIG. 9B is a diagram illustrating a schematic example of the display image according to the fourth modification of the first embodiment.

As illustrated in FIG. 9A and FIG. 9B, the VFG 660 according to the present modification has a form in which rectangles are arranged in a line. In the VFG 660 according to the present modification, when the inserting unit 110 is moved forward, the number of turned on lights changes according to the magnitude of the torque in order from the left end of the VFG, as illustrated in FIG. 9A. By contrast, when the inserting unit 110 is moved backward, the number of turned on lights changes according to the magnitude of the torque in order from the right end of the VFG, as illustrated in FIG. 9B. That is, in the VFG 660 according to the present modification, the reference position of the gauge changes between the case where the inserting unit is moved forward and the case where the inserting unit is moved backward. The load indexes according to the present modification include a forward load index 662 and a backward load index 663 that are provided separately.

The present modification enables use of a larger number of rectangles than that in the case of the first embodiment, and thus enables more detailed expression of the magnitude of the torque than in the case of the first embodiment.

The VFG 660 as in the present modification may be disposed under the character information 620, like the first modification of the first embodiment.

Fifth Modification of the First Embodiment

Figure 10A:
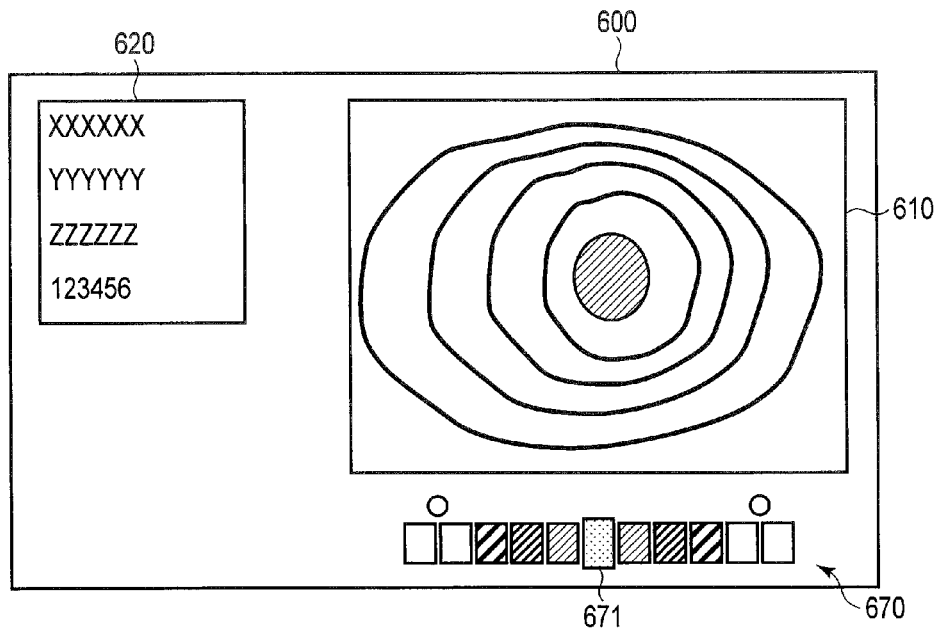
FIG. 10A is a diagram illustrating a schematic example of a display image according to a fifth modification of the first embodiment.
Figure 10B:
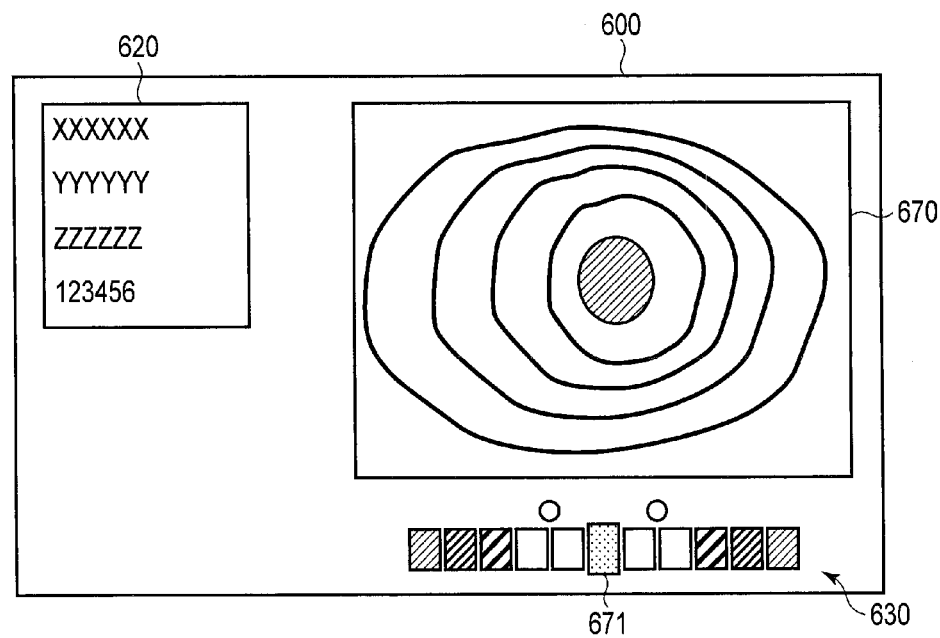
FIG. 10B is a diagram illustrating a schematic example of the display image according to the fifth modification of the first embodiment.

The following is an explanation of a fifth modification of the first embodiment. Only differences of the fifth modification from the first embodiment will be explained hereinafter. The same elements will be denoted by the same reference numerals, and explanation thereof is omitted. The present modification is different from the first embodiment in the form of the VFG in the display image 600. Specifically, as illustrated in FIG. 10A and FIG. 10B, a VFG 670 according to the present modification has a form different from the VFG 630 of the first embodiment, although the VFG 670 is disposed in a position similar to that of the VFG 630 of the first embodiment.

The VFG 670 according to the present modification has a reference rectangle 671 indicating a reference position and aligned with the center of the endoscopic image 610. Specifically, the position of the reference rectangle 671 agrees with an image indicating a moving direction of the inserting unit 110 in the endoscopic image 610. In the VFG 670 according to the present modification, when the inserting unit 110 is moved forward, the form of the rectangles on the right and left sides with the reference rectangle 671 serving as the center changes as illustrated in FIG. 10A, and the number of the changed rectangles corresponds to the torque of the motor 154. By contrast, when the inserting unit 110 is moved backward, the form of the rectangles from the both ends of the VFG 670 toward the reference rectangle 671 changes as illustrated in FIG. 10B, and the number of the changed rectangles corresponds to the torque of the motor 154.

When the inserting unit 110 is moved forward, the fold in the tube displayed in the endoscopic image 610 appears to move from the center toward the peripheral direction. Because the display of the endoscopic image 610 agrees with the direction of the display of the VFG 670 in which the form of the rectangles changes in the right and left directions with the reference rectangle 671 serving as the center, the user can easily recognize the display of the VFG 670. In the same manner, when the inserting unit 110 is moved backward, the fold in the tube displayed in the endoscopic image 610 appears to move from the periphery toward the center. Because the display of the endoscopic image 610 agrees with the direction of the display of the VFG 670 in which the form of the rectangles changes from the right and left ends toward the reference rectangle 671, the user can easily recognize the display of the VFG 670.

Sixth Modification of the First Embodiment

The following is an explanation of a sixth modification of the first embodiment. Only differences of the sixth modification from the first embodiment will be explained hereinafter. The same elements will be denoted by the same reference numerals, and explanation thereof is omitted. In the present modification, a VFG 680 is provided in parallel with the left side of the endoscopic image 610, as illustrated in FIG. 11A and FIG. 11B.

When the inserting unit 110 is moved forward, as illustrated in FIG. 11A, the form of the VFG 680 is changed from the top toward the bottom in accordance with the driving force of the motor 154. By contrast, when the inserting unit 110 is moved backward, as illustrated in FIG. 11B, the form of the VFG 680 is changed from the bottom toward the top in accordance with the driving force of the motor 154.

When attention is paid to the lower part of the endoscopic image 610, when the inserting unit 110 is moved forward, the fold in the tube displayed in the endoscopic image 610 appears to move downward from the center. Because the display of the endoscopic image 610 agrees with the direction of the display of the VFG 680 in which the form of the rectangles changes downward, the user can easily recognize the display of the VFG 680. In the same manner, when attention is paid to the lower part of the endoscopic image 610, when the inserting unit 110 is moved backward, the fold in the tube displayed in the endoscopic image 610 appears to move from the bottom toward the center. Because the display of the endoscopic image 610 agrees with the direction of the display of the VFG 680 in which the form of the rectangles changes upward, the user can easily recognize the display of the VFG 680.

The first embodiment, the fourth modification, and the fifth modification illustrate an example where the VFG is displayed in a position under the endoscopic image 610, but the VFG may be displayed in a position above the endoscopic image 610 or another position as a matter of course.

Second Embodiment

Figure 12B:
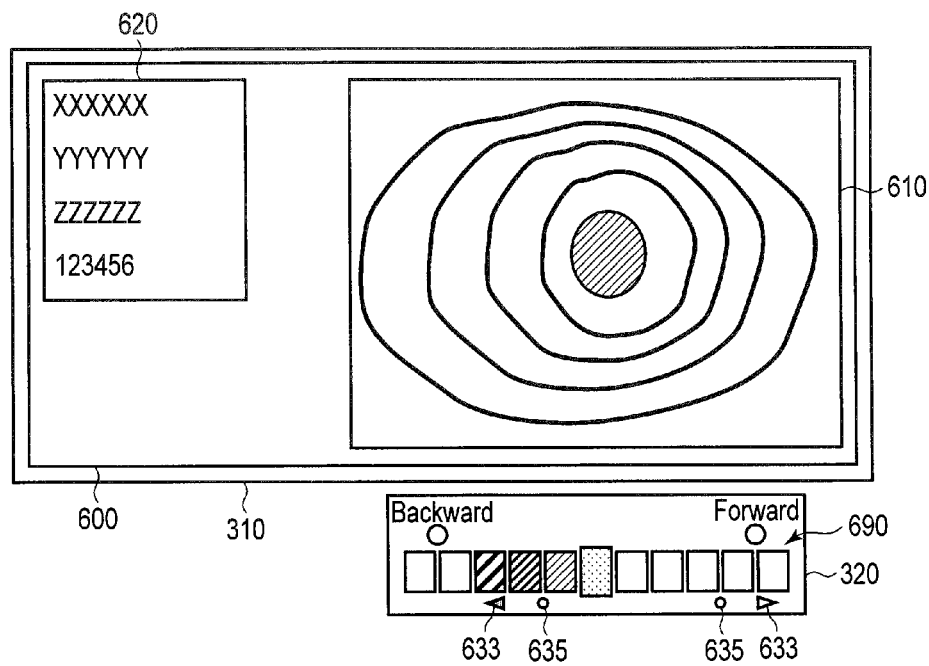
FIG. 12B is a diagram illustrating a schematic example of the display image and the display device displaying the visual force gauge according to the second embodiment.

The following is an explanation of a second embodiment of the present invention. Only differences of the second embodiment from the first embodiment will be explained hereinafter. The same elements will be denoted by the same reference numerals, and explanation thereof is omitted. A VFG 690 according to the present embodiment is not displayed in the display picture 600 on the monitor 310, but is configured to be displayed on a display device 320 attached outside the monitor 310, as illustrated in FIG. 12A and FIG. 12B.

The display device 320 is provided with, for example, a plurality of LEDs 322. In the LEDs 322 of the display device 320, the number of turned on LEDs 322 varies according to the magnitude of the torque of the motor 154. LEDs 322 located on the right side of the reference position are turned on as illustrated in FIG. 12A when the inserting unit 110 is moved forward, and LEDs 322 located on the left side of the reference position are turned on as illustrated in FIG. 12B when the inserting unit 110 is moved backward.

As described above, the present embodiment has the structure in which the VFG 690 is displayed by the display device 320 attached outside the monitor 310, while the first embodiment has the structure in which the VFG 630 is displayed in the display image 600 displayed on the monitor 310. Except for this point, the display contents are the same across the embodiments. As described above, the display device 320 functions as a display device to display the VFG.

Figure 13:
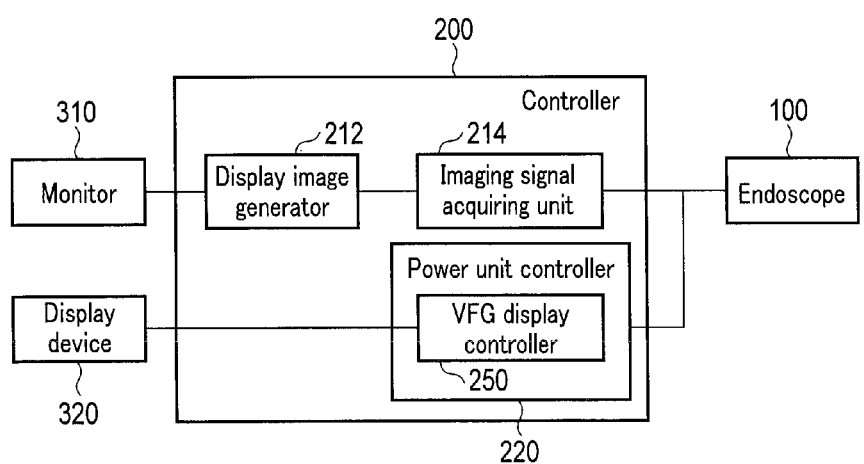
FIG. 13 is a block diagram illustrating a schematic configuration example of a living body insertable apparatus according to the second embodiment.

FIG. 13 illustrates a schematic configuration of a controller 200 according to the present embodiment. As illustrated in FIG. 13, a display image generator 212 is connected with an imaging signal acquiring unit 214, to mainly display an endoscopic image on a monitor 310. By contrast, a VFG display controller 250 in a power unit controller 220 is connected with the display device 320. The VFG display controller 250 controls turning on/off of each of the LEDs 322 of the display device 320.

The present embodiment also enables presentation of the torque applied to the motor 154 to the user, like the first embodiment. In addition, according to the present embodiment, the VFG can be provided outside the monitor 310, without changing the display image 600 displayed on the monitor 310 from a conventional one. FIG. 14A, FIG. 14B, and FIG. 14C illustrate the display device 320 provided outside the monitor 310. The monitor 310 is set on a trolley 311 on which the controller 200 is placed, via an arm 313. The arm 313 is placed at one end on a back surface of the monitor 310 via a fixing mechanism, and placed at the other end on the trolley 311. The arm 313 is movable to change the position of the monitor 310. As illustrated in FIG. 14A, FIG. 14B, and FIG. 14C, the display device 320 is attached to the monitor 310, the trolley 311, the arm 313, and/or the fixing mechanism of the arm 313, with an attachment 315.

Modification of the Second Embodiment

The following is an explanation of a modification of the second embodiment. Only differences of the second modification from the second embodiment will be explained hereinafter. The same elements will be denoted by the same reference numerals, and explanation thereof is omitted. In the present modification, the VFG 690 is not provided on the display device 320 provided outside the monitor 310 as in the second embodiment, but the VFG 690 is provided in a frame portion 314 outside a display area 312 of the monitor 310, as illustrated in FIG. 15A and FIG. 15B. The other structures thereof are the same as those of the second embodiment.

The present embodiment enables unification of the monitor 310 and the display device 320.

The embodiments of the present invention described above include the following inventions.

(1) A display apparatus for a living body insertable apparatus including an inserting unit configured to be inserted into a living body, an imaging unit configured to image an inside of the living body and acquire an image, and a power unit configured to generate a propulsive force for the inserting unit in the living body, the display apparatus comprising:

a driving force detector which acquires a value relating to a driving force of the power unit;

a display calculator which determines a display area of a gauge configured to have the display area varying according to the driving force, based on the value; and a display controller which outputs a signal to display the gauge on a display device, the gauge being displayed in parallel with a predetermined side of the image and having the display area varying along the side.

(2) The display apparatus according to (1), wherein the gauge is provided in parallel with an upper side or a lower side of the image, the gauge includes a first region serving as a region corresponding to a left side of a center of the side, and a second region serving as a region corresponding to a right side of the center, and the display area of the gauge in the first region varies from the center toward the left, and the display area of the gauge in the second region varies from the center toward the right, when the propulsive force acts by the power unit in a direction in which the inserting unit is inserted.

(3) The display apparatus according to (2), wherein the display area of the gauge in the first region varies from left toward the center, and the display area of the gauge in the second region varies from right toward the center, when the propulsive force acts by the power unit in a direction in which the inserting unit is extracted.

(4) The display apparatus according to (1), wherein the gauge is provided in parallel with a left side or a right side of the image, and the display area of the gauge varies from a top toward a bottom, when the propulsive force acts by the power unit in a direction in which the inserting unit is inserted.

(5) The display apparatus according to (4), wherein the display area of the gauge varies from a bottom toward a top, when the propulsive force acts by the power unit in a direction in which the inserting unit is extracted.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A display apparatus for a living body insertable apparatus, the living body insertable apparatus including an inserting unit configured to be inserted into a living body, and a power unit configured to generate a propulsive force for the inserting unit in the living body, the display apparatus comprising:

a controller configured to:

acquire a value relating to a driving force of the power unit;

determine a display area of a gauge based on the value, the display area varying according to the driving force; and output a signal to display the gauge on a display device, wherein the power unit generates a forward propulsive force to propel the inserting unit in a forward direction toward a distal side of the inserting unit, and a backward propulsive force to propel the inserting unit in a backward direction opposite to the forward direction toward a proximal side of the inserting unit, and in the gauge, a direction in which the display area varies when the power unit generates the forward propulsive force is opposite to a direction in which the display area varies when the power unit generates the backward propulsive force, wherein the controller is further configured to, as initial correction processing:

acquire individual information of the power unit stored in the power unit, the individual information relating to individual variation of a relation between the value relating to the driving force and the display area;

correct a calculation expression representing a relation between the value relating to the driving force and the display area; and determine the display area based on the calculation expression.

2. The display apparatus according to claim 1, wherein the controller is configured to display the gauge only when the power unit operates.

3. The display apparatus according to claim 1, wherein the controller is configured to display the gauge with an index serving as a mark for the display area.

4. The display apparatus according to claim 1, wherein the inserting unit further includes an imaging unit configured to image an inside of the living body and acquire an image, and the controller is configured to display the gauge with the image.

5. A display apparatus for a living body insertable apparatus, the living body insertable apparatus including an inserting unit configured to be inserted into a living body, and a power unit configured to generate a propulsive force for the inserting unit in the living body, the display apparatus comprising:

a controller configured to:

acquire a value relating to a direction of a driving force of the power unit;

determine a display configuration of a gauge configured to have the display configuration varying according to the direction of the driving force, based on the value; and output a signal to display the gauge on a display device, wherein the power unit generates a forward propulsive force to propel the inserting unit in a forward direction toward a distal side of the inserting unit, and a backward propulsive force to propel the inserting unit in a backward direction opposite to the forward direction toward a proximal side of the inserting unit, in the gauge, a the display configuration varies according to whether the driving force is a forward driving force relating to the forward propulsive force or a backward driving force relating to the backward propulsive force; and the controller is further configured to, as initial correction processing:

acquire individual information of the power unit stored in the power unit, the individual information relating to individual variation of a relation between the value relating to the driving force and the display configuration;

correct a calculation expression representing a relation between the value relating to the driving force and the display configuration; and determine the display configuration based on the calculation expression.

* * * * *